United States Patent [19]
O'Donnell, Jr.

[11] Patent Number: 5,643,250
[45] Date of Patent: Jul. 1, 1997

[54] LASER PROBE HAND PIECE

[76] Inventor: Francis E. O'Donnell, Jr., 709 The Hamptons La., Town & Country, Mo. 63017

[21] Appl. No.: 489,477

[22] Filed: Jun. 12, 1995

Related U.S. Application Data

[63] Continuation-in-part of Ser. No. 238,799, May 6, 1994, abandoned, which is a continuation of Ser. No. 925,873, Aug. 7, 1992, abandoned.

[51] Int. Cl.⁶ ............................. A61N 5/06; A61B 17/36
[52] U.S. Cl. ..................................... 606/4; 606/12
[58] Field of Search ................................. 606/14, 15, 16, 606/17, 10, 11, 12, 4, 5, 6

[56] References Cited

U.S. PATENT DOCUMENTS

| | | |
|---|---|---|
| 4,438,765 | 3/1984 | Wilinsky . |
| 4,744,360 | 5/1988 | Bath . |
| 4,846,172 | 7/1989 | Berlin . |
| 4,860,743 | 8/1989 | Abela ........................ 606/15 |
| 4,880,001 | 11/1989 | Weinberg . |
| 5,071,422 | 12/1991 | Watson et al. . |
| 5,112,328 | 5/1992 | Taboada et al. . |
| 5,123,902 | 6/1992 | Muller et al. ........................ 606/21 |

FOREIGN PATENT DOCUMENTS

| | | |
|---|---|---|
| 0335714 | 10/1989 | Germany . |
| 3822011 | 1/1990 | Germany . |

*Primary Examiner*—Lee S. Cohen
*Assistant Examiner*—Sonya Harris-Ogugua
*Attorney, Agent, or Firm*—Paul M. Denk

[57] ABSTRACT

A laser probe hand piece for use in laser eye surgery is disclosed having a housing fiber optic energy being fiber housed therein. The housing includes a infusion port whereby irrigating solution can be infused into the eye to cool and irrigate the surgical area, and the housing also houses an aspiration means whereby fluid and excised tissue can be aspirated from the surgical field. The laser probe hand piece and associated console employ a feedback loop cutoff whereby the laser energy is cut off if the laser is not in contact with the target tissue.

15 Claims, 2 Drawing Sheets

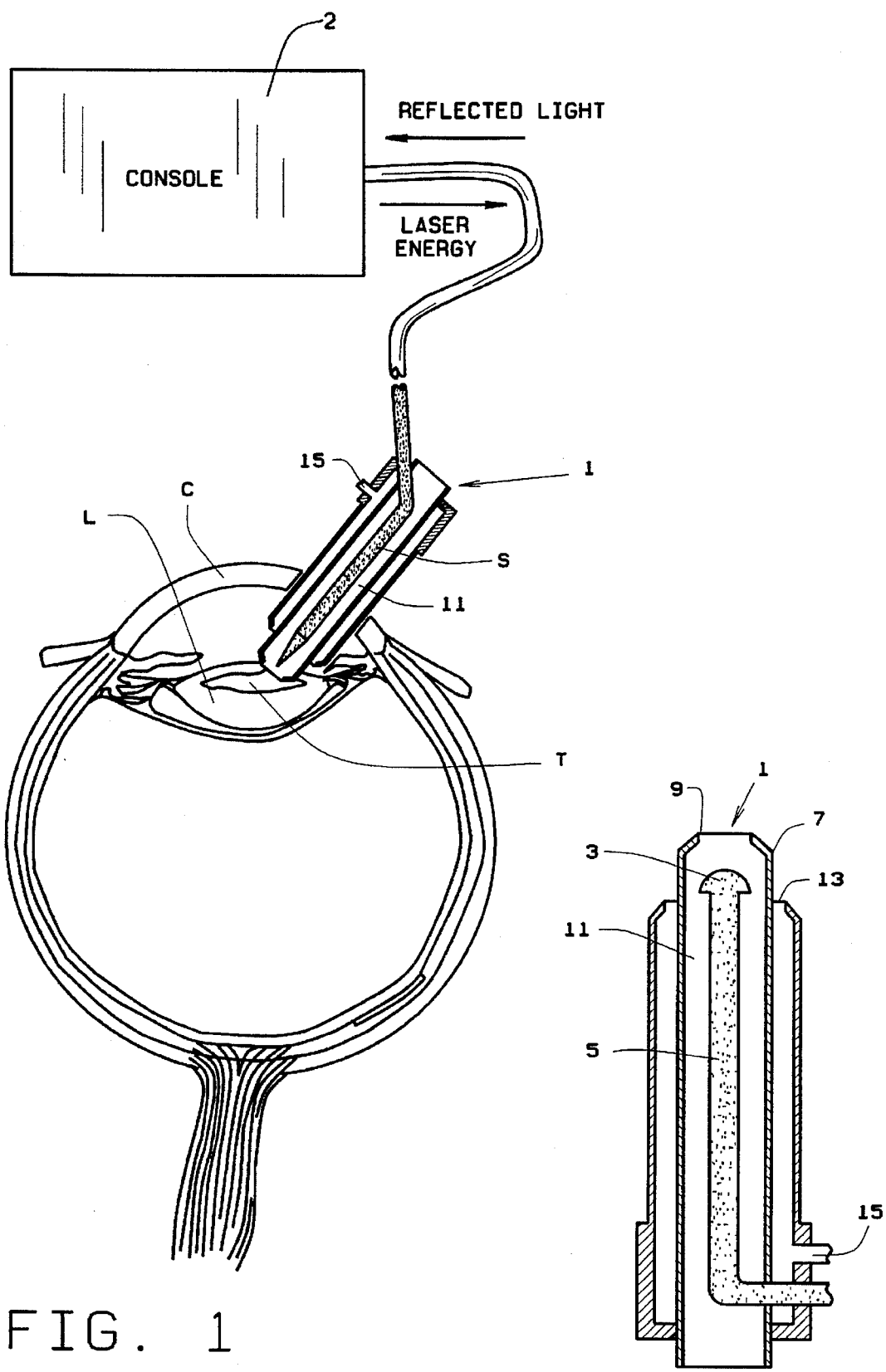

5,643,250

LASER PROBE HAND PIECE

This application is a continuation-in-part of application Ser. No. 08/238,799, filed May 6, 1994, which is a 1.62 continuation of Ser. No. 07/925,873 filed on Aug. 7, 1992 both abandoned.

BACKGROUND OF THE INVENTION

This invention relates to a laser probe hand piece used in eye surgery, and more specifically to a laser probe hand piece device used for ablating a cataract as well as a console for providing laser energy, with the hand piece providing for irrigation and suction of the surgical field as well as providing the laser energy for such applications. The hand piece and console provide a feedback loop to terminate the laser energy when the hand piece is not in contact with cataract tissue.

SUMMARY OF THE INVENTION

It is therefore the object of the invention to provide a unitary laser probe hand piece that delivers laser energy as well as providing irrigation and aspiration ports thereon within an integral unit.

Another object of the invention is to provide a laser probe hand piece that can have a variety of shapes, including variations in the location of the opening for emitting the laser energy, as well as providing the integral and proximate aspiration and irrigation ports.

Still another object of the invention is to provide a laser probe hand piece that can deliver ultraviolet or infrared energy with either a continuous of pulse mode.

Yet another object of the invention is to provide a laser probe hand piece that contains reflected light feedback loop that cuts off the laser unless the laser energy is in contact with the target tissue.

Briefly state, a laser probe hand piece that can deliver an infrared or ultraviolet radiation in either a continuous wave of pulse mode having an irrigation port in an aspiration port formed therein, or preferably concentric therewith. The probe tip can be transparent thereby allowing better lighting and visualization of the operative area. The laser probe and associated console also contain a feedback loop that cuts off the laser energy unless the laser energy is in contact with target tissue.

BRIEF DESCRIPTION OF THE DRAWINGS

FIG. 1 is a cross-sectional view of the laser probe hand piece and console of the present invention, the laser probe hand piece inserted through the cornea and directed to the cataract tissue with the lens of the eye;

FIG. 2 is a cross-sectional view of one embodiment from the laser probe hand piece of the present invention;

Corresponding reference numerals indicate corresponding elements throughout the various drawings.

DESCRIPTION OF THE PREFERRED EMBODIMENT

Figures 3, 4, 5:
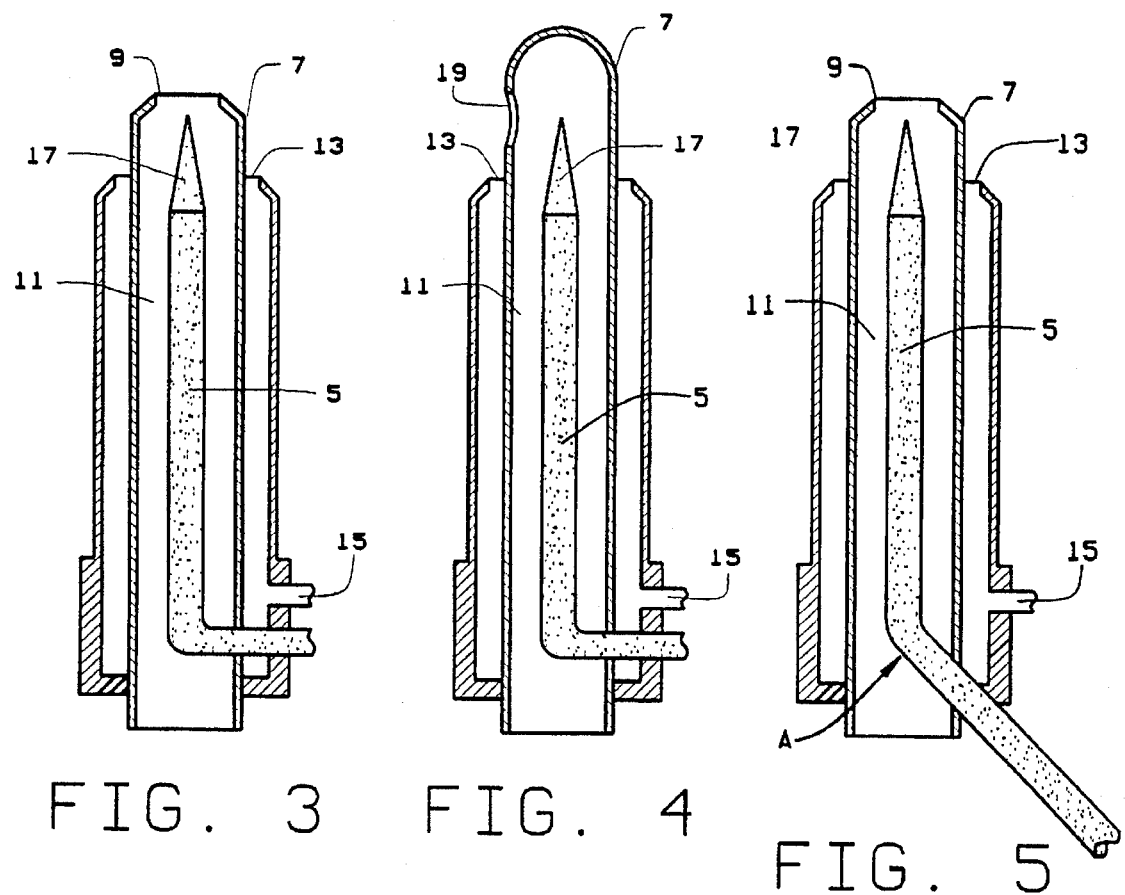
FIG. 3 is a cross-sectional view of another embodiment of the laser probe hand piece of the present invention.
FIG. 4 is a cross-sectional view of yet another embodiment of the laser probe hand piece of the present invention.
FIG. 5 is a cross-sectional view of the embodiment of the laser probe hand piece as shown in FIG. 1.

Referring now to the drawings, particularly FIG. 1, a laser probe hand piece of the present invention is shown generally at 1 inserted through the cornea C of an eyeball. The tip of the probe is placed into lens L and aimed at cataract tissue T.

The laser probe hand piece 1 of the present invention can have a variety of configurations without departing from the scope of the invention as illustrated by FIGS. 2 through 4. The laser probe hand piece is connected to a console 2. Console 2 provides a source of laser energy to hand piece 1. Furthermore, console 2 houses a reflected-light feedback loop designed to cut off the laser energy that will be described in greater detail below.

Referring now to FIG. 2, hand piece 1 is shown with a convex sapphire tip 3 attached to quartz fiber 5. Fiber 5 understandably leads to an energy laser source (not shown). The laser energy source provides appropriate laser energy, for example, ultraviolet (e.g. 308 NM) or infrared (e.g. 1064 NM YAG or erbium. In a continuous wave or pulse mode. Alternatively, the wave length could be 810 NM from a diode laser.

Tip 7 can be made of metal of any other appropriate material, but preferably would be transparent glass or polymer (with or without infrared absorbing ability) so that the surgeon can best visualize the target tissue. FIG. 2 has opening 9 through which the laser beam is directed. Opening 9 also serves as an aspiration port through which suction is applied to aspirate fluid and tissue into aspiration chamber 11 and out of the device through tubing or other appropriate means (not shown). Port 13 functions as an infusion port. An appropriate irrigating solution, such as balanced salt solution, enters device 1 through port 15. This solution is used to irrigate the operative area, to cool the tissue, and to flush away cataract tissue debris. The irrigating solution, as well as tissue, is aspirated through opening 9, as previously explained, and removed from the surgical field in that manner.

One alternative embodiment, as illustrated in FIG. 3, employs a conical sapphire tip 17. A third alternative embodiment, as shown in FIG. 4, employs a side opening 19 formed within tip 7. It should be noted again that the alternative embodiments are for illustrative purposes only and do not depart from the scope of this invention. For example, the opening in tip 7, as shown as end opening 9 in FIGS. 2 and 3 can be side opening, as illustrated in FIG. 4, or even a beveled tip 7 (not shown).

FIG. 5 better illustrates the embodiment of the laser hand piece 1 of the present invention shown in FIG. 1. It will be appreciated that the fiber 5 enters the hand piece at a greater angle A than in the previously described hand pieces. In this case, the angle of the laser may be approximately 60°. Although the previously described hand pieces function well, the design of FIG. 5 lessens the likelihood that fiber 5 will not properly reflect light off its internal walls.

The quartz fiber 5 can be bare, sculpted, or have various shaped sapphire tips as illustrated in FIGS. 2–4.

Figure 6:
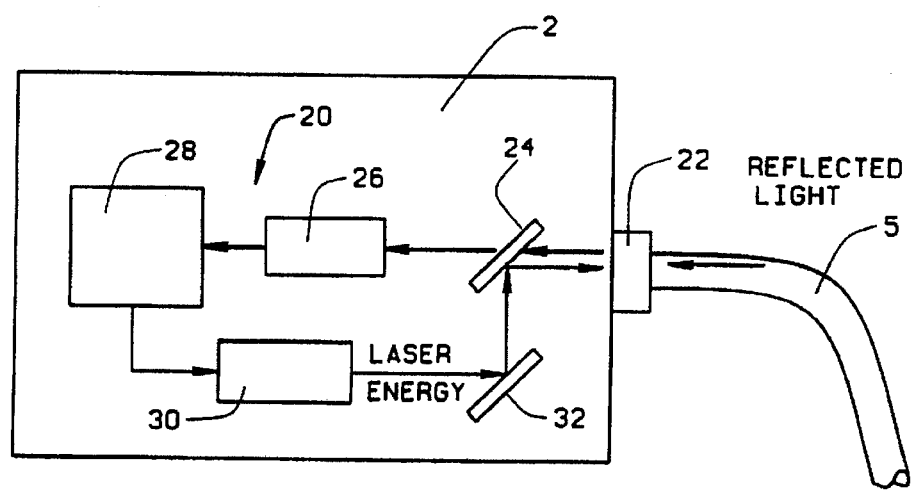
FIG. 6 is a partial schematic, partial block diagram illustrating the feedback loop of the present invention.

It should be noted that the invention contains a feedback loop means for cutting the laser off unless the tip of the laser is in contact with the target tissue. This feedback loop means, best illustrated in FIG. 6, employs a helium neon or diode laser aiming beam to sense the target tissue. The feedback loop, indicated generally be reference numeral 20, is housed in console 2. Feedback loop 20 has an optic fiber connector 22 for the connection of fiber 5. The remainder of the loop consists of a first transparent mirror 24, a spectrometer 26, a microprocessor 28, a laser cavity 30 and a second transparent mirror 32. Reflected light enters loop 20 via optical fiber 5. The light is reflected from the target tissue. The wavelength and intensity of the reflected light varies according to the presence or absence of target tissue as well as the nature of that tissue. The reflected light passes through transparent mirror 24. The reflected light enters spectrometer 26. Spectrometer 26 constantly samples the reflected light and identifies the wavelength and intensity. This information is fed to microprocessor 28 which controls the laser energy output from laser cavity 30 in response to preprogrammed criteria. The laser energy is directed to optic fiber 5 by mirrors 32 and 24. If the reflected light analysis indicates that the laser energy is not striking target tissue, the laser energy will be shut off.

The previous detailed description is intended for an illustrative purposes only and is not intended in a limiting sense.

Having thus described the invention, what is claimed and desired to be secured by Letters Patent is:

1. A laser probe hand piece utilizing laser energy for the surgical destruction and removal of cataract from the lens of an eye, while supplying an irrigating fluid thereto, comprising:

a hand piece, said hand piece having a front thereof;

a housing formed in said hand piece;

a fiber optic fiber disposed within said housing for conducting laser energy so as to break down the cataract tissue during functioning;

an energy source for delivering laser energy to the fiber optic fiber;

a housing means surrounding said housing and provided for introducing an irrigating solution to the cataract tissue during surgery;

means located on said housing for aspirating such irrigation solution and cataract tissue from the lens;

said hand piece housing cooperating with said aspirating means for aspirating such irrigating solution and cataract tissue from the lens of the eye;

said fiber optic fiber having a forwardly disposed end provided proximate the front of the hand piece and within said housing, and a sapphire laser tip provided connecting to the forwardly disposed end of the fiber optic fiber for focusing the conducted laser energy at the cataract to break down the cataract tissue, said housing means having a port formed therein, said port disposed to allow a flow of irrigating solution through said housing means to the cataract tissue, said port operatively connected to a suction device, thereby providing aspiration;

said fiber optic fiber is quartz and the sapphire laser tip being sculpted; and a feedback loop means for shutting off that energy source unless the laser probe is in contact with such cataract tissue.

2. The invention of claim 1 wherein the laser energy source provides ultraviolet energy.

3. The invention of claim 1 wherein the laser energy source is infrared energy.

4. The invention of claim 3 wherein the wave length is 308 NM.

5. The invention of claim 1 wherein the laser energy source is delivered in the continuous mode.

6. The invention of claim 1 wherein the laser energy is provided in a pulse mode.

7. The invention of claim 1 wherein the feedback loop means further comprises means for analyzing a reflected beam to sense a contiguity of the cataract tissue.

8. The invention of claim 7 wherein the feedback loop means for shutting off said energy source further comprises a reflected light analysis means, said reflected light analyzing means located in a console, said reflect light analyzing means exposed to the reflectance of said laser energy reflected from such cataract tissue, said reflected light analyzing means disposed so as to shut off said energy source when the reflectance of the tissue decreases.

9. The invention of claim 8 wherein said reflected light analyzing means is programmable so as to discontinue said laser energy if the reflected light indicates that the laser energy is not contacting a target tissue.

10. A laser probe for the surgical destruction and removal of cataract from the lens of an eye comprising:

a hand piece;

a fiber optic fiber disposed within said hand piece for the delivery of a laser energy so as to break down the cataract tissue;

an energy source;

means integrally on said hand piece for introducing irrigating solution to such cataract tissue during surgery;

means integrally on said hand piece for aspirating such irrigating solution and cataract tissue from the lens; and feedback loop means for shutting off said energy source unless the laser probe is in contact with such cataract tissue.

11. The invention of claim 10 wherein the feedback loop means further comprises a reflectant aiming beam to sense the cataract tissue.

12. The invention of claim 11 wherein the aiming beam further comprises a helium neon beam or diode laser.

13. The invention of claim 12 wherein the feedback loop means for shutting off said energy source further comprises a reflection determining means, said reflection determining means located in said hand piece, said reflection determining means disposed to the reflectance of a aiming beam reflected from such cataract tissue, reflectance determining means disposed so as to shut off said energy source when the reflectance of the tissue decreases.

14. A method of ablating cataract tissue in the lens of an eye, comprising:

inserting a laser probe into such lens;

positioning the laser probe against the cataract tissue;

activating the laser energy;

instilling irrigating solution on and around the cataract tissue through said probe so as to cool and to suspend such cataract tissue;

destroying such cataract tissue;

aspirating such irrigating solution and destroying cataract tissue from the lens through an aspiration port located on said laser probe;

discontinuing the laser energy;

withdrawing the laser probe from the eye; and using an aiming feedback loop to sense the cataract tissue.

15. The method of claim 14 comprising automatically cutting off of said laser energy when the laser probe is not sensing the cataract tissue.

* * * * *